United States Patent
Ozawa et al.

(10) Patent No.: US 11,314,179 B2
(45) Date of Patent: Apr. 26, 2022

(54) POLYESTER RESIN, METHOD FOR PRODUCING POLYESTER RESIN, AND TONER USING SAID POLYESTER RESIN

(71) Applicant: Mitsubishi Chemical Corporation, Chiyoda-ku (JP)

(72) Inventors: Tadahiro Ozawa, Tokyo (JP); Asako Kaneko, Tokyo (JP); Masaaki Kiura, Tokyo (JP); Yoshihiro Kamon, Tokyo (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 15/573,373

(22) PCT Filed: May 13, 2016

(86) PCT No.: PCT/JP2016/064303
§ 371 (c)(1),
(2) Date: Nov. 10, 2017

(87) PCT Pub. No.: WO2016/186028
PCT Pub. Date: Nov. 24, 2016

(65) Prior Publication Data
US 2018/0067412 A1 Mar. 8, 2018

(30) Foreign Application Priority Data
May 15, 2015 (JP) .............................. JP2015-099639

(51) Int. Cl.
| | |
|---|---|
| *G03G 9/087* | (2006.01) |
| *C08G 63/688* | (2006.01) |
| *C08G 63/672* | (2006.01) |
| *C07D 515/04* | (2006.01) |
| *C08G 63/181* | (2006.01) |
| *G01R 33/46* | (2006.01) |

(52) U.S. Cl.
CPC ....... *G03G 9/08755* (2013.01); *C07D 515/04* (2013.01); *C08G 63/181* (2013.01); *C08G 63/672* (2013.01); *C08G 63/688* (2013.01); *C08G 63/6884* (2013.01); *C08G 63/6886* (2013.01); *G03G 9/087* (2013.01); *G01R 33/46* (2013.01)

(58) Field of Classification Search
CPC .. C07D 515/04; C08G 63/181; C08G 63/672; C08G 63/688; C08G 63/6884; C08G 63/6886; G03G 9/087; G03G 9/08755
See application file for complete search history.

(56) References Cited

U.S. PATENT DOCUMENTS

| | | | | |
|---|---|---|---|---|
| 6,025,061 A | * | 2/2000 | Khanarian | C08G 63/668 428/221 |
| 6,063,464 A | * | 5/2000 | Charbonneau | C08G 63/668 428/36.92 |
| 6,140,003 A | * | 10/2000 | Sacripante | G03G 9/08755 430/108.22 |
| 6,368,710 B1 | | 4/2002 | Hayes | |
| 2004/0024102 A1 | * | 2/2004 | Hayes | C08L 69/00 524/445 |

(Continued)

FOREIGN PATENT DOCUMENTS

| | | |
|---|---|---|
| EP | 1 772 778 A2 | 4/2007 |
| JP | 11-506484 | 6/1999 |

(Continued)

OTHER PUBLICATIONS

Nicolas Descamps et al "Isothermal Crystallization Kinetics of Poly(ethylene terephthalate) Copolymerized with Various Amounts of Isosorbide", Feb. 5, 2020 (Year: 2020).*

(Continued)

*Primary Examiner* — Ling Siu Choi
*Assistant Examiner* — Gennadiy Mesh
(74) *Attorney, Agent, or Firm* — Oblon, McClelland, Maier & Neustadt, L.L.P.

(57) ABSTRACT

A polyester resin having low-temperature (80-240° C.) fluidity, storage stability, and achieving both dispersibility and grindability, where the polyester resin includes, in reacted form: a polyhydric alcohol; a polycarboxylic acid; a sulfonate component, which is a bis(2-hydroxyethyl)isophthalate sulfonic acid salt; and a hetero alicyclic skeleton, which can be a monomer of formula (1) and/or formula (2):

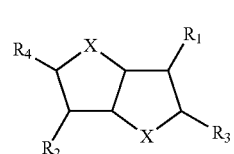

(1)

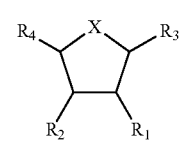

(2)

where X is O, S, or NH and $R_1$ to $R_4$ are functional groups. Also, a method for producing the polyester resin by polymerizing a mixture containing the polyhydric alcohol, the polycarboxylic acid, the sulfonate component and the hetero alicyclic skeleton component having formula (1) and/or (2).

22 Claims, No Drawings

(56) References Cited

U.S. PATENT DOCUMENTS

| | | | |
|---|---|---|---|
| 2007/0007751 A1 | 4/2007 | Nosella et al. | |
| 2012/0156607 A1* | 6/2012 | Farrugia | G03G 9/08791 |
| | | | 430/108.4 |
| 2012/0276478 A1* | 11/2012 | Wosnick | G03G 9/08795 |
| | | | 430/109.4 |
| 2012/0276479 A1* | 11/2012 | Yoo | G03G 9/08775 |
| | | | 430/109.4 |
| 2014/0302435 A1* | 10/2014 | Veregin | G03G 9/1133 |
| | | | 430/110.2 |
| 2015/0291730 A1 | 10/2015 | Tamura et al. | |
| 2018/0067412 A1* | 3/2018 | Ozawa | C08G 63/688 |

FOREIGN PATENT DOCUMENTS

| | | | |
|---|---|---|---|
| JP | 2003-212985 | | 7/2003 |
| JP | 2007-102224 | | 4/2007 |
| JP | 2008-506022 | | 2/2008 |
| JP | 2008-115244 | A | 5/2008 |
| JP | 2010-285555 | | 12/2010 |
| JP | 2013-256599 | | 12/2013 |
| JP | 2014-40517 | | 3/2014 |
| JP | 2014-040517 | * | 6/2014 |
| JP | 5637497 | B2 | 12/2014 |
| JP | 2015-131438 | | 7/2015 |
| WO | 96/36657 | A1 | 11/1996 |
| WO | 2006/010063 | A1 | 1/2006 |
| WO | 2014/088097 | A1 | 6/2014 |
| WO | 2015/163400 | A1 | 10/2015 |

OTHER PUBLICATIONS

Yu et al "Relationship between Physical Properties and Chemical Structures of Poly(ethylene terephthalate-co-ethylene isophthalate)", Journal of Applied Polymer Science, vol. 73, 1191-1195 (1999) (Year: 1999).*

Matthew G. McKee et al"Branched polyesters: recent advances in synthesis and performance", Prog. Polym. Sci. 30 (2005) 507-539 (Year: 2005).*

International Search Report dated Aug. 16, 2016 in PCT /JP2016/064303 Filed May 13, 2016.

Extended European Search Report dated Mar. 12, 2018 in Patent Application No. 16796421.2, 7 pages.

Korean Office Action dated Mar. 12, 2018 in Patent Application No. 10-2017-7032301 (with English translation), 19 pages.

Combined Chinese Office Action and Search Report dated May 5, 2019 in Patent Application No. 201680027475.7, 13 pages (with unedited computer generated English translation).

Notice of Reasons for Refusal dated Oct. 29, 2019, in Japanese Patent Application No. 2016-534263 filed May 13, 2016 (with English translation).

* cited by examiner

POLYESTER RESIN, METHOD FOR PRODUCING POLYESTER RESIN, AND TONER USING SAID POLYESTER RESIN

TECHNICAL FIELD

The present invention relates to a polyester resin, a method for producing a polyester resin, and a toner using the polyester resin.

This application is based upon and claims the benefit of priority of the prior Japanese Patent Application No. 2015-099639, filed on May 15, 2015, the entire contents of which are incorporated herein by reference.

BACKGROUND ART

In methods of obtaining an image by using an electrophotographic printing method and an electrostatic imaging method, electrostatically charged images formed on a photoreceptor are developed by a toner that is electrically charged in advance by friction, and then the images are fixed. Examples of image-fixing methods include a heat roller technique of fixing a toner image obtained by development by using a pressurized and heated roller and a non-contact fixing technique of fixing a toner image by using an electric oven or flash beam light. In order to pass through these processes without any problem, a toner is required first to maintain a stable charged amount and then to have favorable fixability onto paper. Further, since an apparatus includes a fixing unit as a heated body and the temperature in the apparatus increases, it is necessary to prevent toner blocking.

Moreover, no smudges on the apparatus and no overlapping results on the printed surface should appear during continuous printing operations, that is, toner durability is required. A binder resin for a toner is a material that greatly affects the toner characteristics as described above, and examples of the binder resin which is known include a polystyrene resin, a styrene-acrylic resin, a polyester resin, an epoxy resin, and a polyamide resin. However, recently, attention has been drawn particularly to a polyester resin which is excellent in toughness, fixability at a low temperature, and the like and has favorable performance balance. As a method for producing a toner using a polyester resin, a grinding method, a chemical method, and the like are exemplified. The grinding method is a method in which a polyester resin, a pigment (colorant) and a release agent or the like are melt-kneaded, the obtained kneaded product is finely pulverized by a pulverizer or the like and then classified to thereby obtain a toner, and the grinding method is widely used in industrial application. In recent years, in order to realize high-quality image formation of an image to be formed, a decrease in particle diameter of a toner has been demanded. However, since energy and time required for pulverizing are increased, production processes are cumbersome, and a yield is lowered in the grinding method, a problem arises in that production costs are significantly increased. Therefore, attention has been drawn to a chemical method by which a decrease in particle diameter can be achieved more efficiently.

As the chemical method, for example, there is mentioned a method in which a polyester resin and a material containing other toner blending materials are dissolved or dispersed in an organic solvent capable of dissolving the polyester resin, this solution is dispersed in an aqueous medium containing a dispersion stabilizer or the like and granulated, the organic solvent is then removed, and the obtained particles are washed and dried to obtain toner particles. In the case of using an organic solvent, a step of removing a solvent is necessary, and thus the chemical method is a technique with large environmental load. In a case where production is conducted with a small amount of a solvent, the viscosity is increased so that the particle diameter is likely to increase and high-quality image formation that is a merit of the chemical method is likely to degrade.

Further, in a case where production of a chemical toner is conducted directly in water by using a surfactant or an emulsifier, there is a tendency that moisture adsorption to the toner after drying is likely to occur and storage stability degrades.

Therefore, from the viewpoint of reducing environmental load, there is a demand for a water-dispersible polyester resin for a chemical toner in which a specific particle diameter is shown in a simple manner by treating a resin and water with heat, pressure, or the like without use of an organic solvent, a surfactant, and an emulsifier and which has favorable water dispersibility.

In addition, from the viewpoint of energy saving in production processes, there is a demand for a resin by which pulverization energy can be decreased and water dispersion treatment time in accordance with a decrease in particle diameter can be shortened, as long as the resin is a resin having favorable grindability.

For example, Patent Literature 1 describes that a toner excellent in fusion performance characteristics and electric performance characteristics is obtainable by using a water-dispersible polyester resin obtained by copolymerizing dimethyl terephthalate/sodium 5-sulfoisophthalate/propylene glycol/dipropylene glycol in the presence of a butyltin oxide catalyst.

Patent Literature 2 describes that a coating film excellent in tone and water resistance is obtainable by preparing an aqueous resin solution subjected to neutralization treatment, by using a polyester resin obtained by copolymerizing terephthalic acid/isophthalic acid/sodium 5-sulfoisophthalate/ethylene glycol in the presence of tetrabutyl titanate.

Patent Literatures 3 and 4 describe that a resin for a toner excellent in grindability is obtainable by copolymerizing isosorbide and erythritane.

CITATION LIST

Patent Literature

Patent Literature 1: JP 2007-102224 A
Patent Literature 2: JP 2003-212985 A
Patent Literature 3: JP 2010-285555 A
Patent Literature 4: JP 2013-256599 A

SUMMARY OF THE INVENTION

Problem to be Solved by the Invention

However, since the polyester resins described in Patent Literatures 1 and 2 do not have a hetero alicyclic structure such as isosorbide or erythritane, the grindability of the resins are not sufficient. Since the polyester resins described in Patent Literatures 3 and 4 do not have a sulfonic acid salt structure, the water dispersibility of the resins is not sufficient.

An object of the invention is to provide a polyester resin in which a balance between water dispersibility and grindability can be achieved and which is excellent in low-temperature fluidity and storage stability.

Means for Solving Problem

[1] A polyester resin containing a sulfonate component and a hetero alicyclic skeleton component as constituent units.

[2] The polyester resin described in [1], in which the sulfonate component is a component derived from a bis(2-hydroxyethyl)phthalate sulfonic acid salt.

[3] The polyester resin described in [1], in which the hetero alicyclic skeleton component is at least one monomer selected from compounds represented by the following General Formulae (1) and (2).

[Chem. 1]

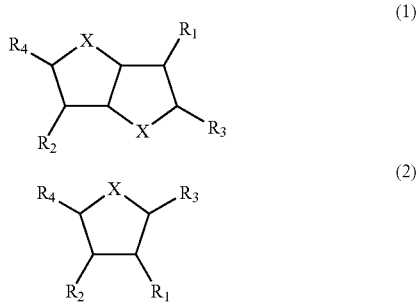

In General Formulae (1) and (2), X is selected from O, S, and SH; $R_1$ and $R_2$ each independently represent a functional group selected from the group consisting of a hydroxyl group, a hydroxyalkyl group, a hydroxyalkyl ether group, a carboxyl group, an amine group, an acid amide group, an alkoxy group, a carboxylic acid ester group, a carboxylic acid halide, a thiol group, and a phosphoric acid group, and $R_1$ and $R_2$ may be the same as or different from each other; and $R_3$ and $R_4$ each independently represent a functional group selected from the group consisting of a hydrogen atom, an alkyl group, an alkenyl group, a hydroxyl group, a hydroxyalkyl group, an aminoalkyl group, a carboxyl group, an amine group, an acid amide group, an alkoxy group, a carboxylic acid ester group, a carboxylic acid halide, a thiol group, and a phosphoric acid group, and $R_3$ and $R_4$ may be the same as or different from each other.

[4] The polyester resin described in [1] or [2], in which the hetero alicyclic skeleton component is at least one kind selected from isosorbide and erythritane.

[5] The polyester resin described in any one of [1] to [3], in which a counterion of a sulfonic acid salt contains at least one kind selected from sodium, potassium, and lithium.

[6] A toner containing the polyester resin described in any one of [1] to [4].

[7] A method for producing a polyester resin in which polymerization is performed in the presence of a mixture of a sulfonic acid salt and at least one kind of a monomer selected from compounds represented by the following General Formulae (1) and (2).

[Chem. 1]

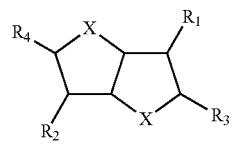

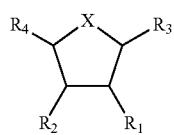

In General Formulae (1) and (2), X is selected from O, S, and NH; $R_1$ and $R_2$ each independently represent a functional group selected from the group consisting of a hydroxyl group, a hydroxyalkyl group, a hydroxyalkyl ether group, a carboxyl group, an amine group, an acid amide group, an alkoxy group, a carboxylic acid ester group, a carboxylic acid halide, a thiol group, and a phosphoric acid group, and $R_1$ and $R_2$ may be the same as or different from each other; and $R_3$ and $R_4$ each independently represent a functional group selected from the group consisting of a hydrogen atom, an alkyl group, an alkenyl group, a hydroxyl group, a hydroxyalkyl group, an aminoalkyl group, a carboxyl group, an amine group, an acid amide group, an alkoxy group, a carboxylic acid ester group, a carboxylic acid halide, a thiol group, and a phosphoric acid group, and $R_3$ and $R_4$ may be the same as or different from each other.

[8] The polyester resin described in [1], in which the polyester resin contains a hetero alicyclic skeleton unit in 1 part by mole or more and 90 parts by mole or less with respect to 100 parts by mole of a repeating unit derived from polycarboxylic acid.

[9] A polyester resin in which after 5 g±0.5 g of a resin, which is dried with a resin obtained by freeze-drying a water dispersion in the presence of an aggregating agent, is stored for 24 hours in a constant temperature-and-humidity machine adjusted to a temperature of 40° C. and a humidity of 80%, a proportion of the resin passing through a sieve having a mesh size of 2 mm is 80 wt % or more.

[10] The polyester resin described in [1], in which a softening temperature is 80° C. or higher and 160° C. or lower.

[11] The polyester resin described in [1], in which a sulfonic acid salt component is contained in 2 parts by mole or more and 20 parts by mole or less with respect to 100 parts by mole of a repeating unit derived from polycarboxylic acid.

[12] The method for producing a polyester resin described in [7], in which the polyalcohol represented by the above General Formula (1) or (2) is contained in 1 part by mole or more and 90 parts by mole or less in the monomer mixture with respect to 100 parts by mole of polycarboxylic acid.

[13] A method for producing the polyester resin described in [7], in which the sulfonic acid salt is contained in 2 parts by mole or more and 20 parts by mole or less in the monomer mixture with respect to 100 parts by mole of polycarboxylic acid.

[14] A method for producing the polyester resin described in [7], in which a monomer having three or more functional groups is contained in 1 part by mole or more and 30 parts by mole or less in the monomer mixture with respect to 100 parts by mole of polycarboxylic acid.

[15] A method for producing the polyester resin described in [14], in which the monomer having three or more functional groups is trimellitic acid or an acid anhydride thereof, or trimethylol propane.

[16] A method for producing the polyester resin described in [7], in which a release agent is contained in the monomer mixture.

Effect of the Invention

In the case of using the polyester resin of the invention in a toner, it is possible to provide a toner in which a balance between water dispersibility and grindability can be achieved and which is excellent in low-temperature fluidity and storage stability.

MODE(S) FOR CARRYING OUT THE INVENTION

Polyester Resin

A polyester resin contains a sulfonic acid salt component and a hetero alicyclic skeleton component as constituent units.

Incidentally, in the present specification, the fact that the polyester resin "contains (a component) as a constituent unit" means that the polyester resin contains a constituent unit derived from the component (compound).

The polyester resin of the invention may be obtained by polymerizing a sulfonic acid salt and a compound having a hetero alicyclic skeleton according to a known polyester polymerization method.

Sulfonic Acid Salt Skeleton Component

A sulfonic acid salt skeleton component of the invention is a component derived from a polyfunctional (polyhydric) acid, alcohol, or hydroxy acid that constitutes the polyester resin.

Examples of a compound having a sulfonic acid salt skeleton include bis(2-hydroxyethyl)phthalate sulfonic acid salts such as sodium 2-sulfoisophthalate dihydroxyethyl ester, sodium 4-sulfoisophthalate dihydroxyethyl ester, sodium 5-sulfoisophthalate dihydroxyethyl ester, and sodium 6-sulfoisophthalate dihydroxyethyl ester. Among the above-described compounds, from the viewpoint of raw material availability and polymerization stability, it is preferable to use sodium 5-sulfoisophthalate dihydroxyethyl ester. As counterion species, sodium, potassium, lithium, and the like can be appropriately selected. For example, sodium 5-sulfoisophthalate dihydroxyethyl ester that is easily available may be ion-exchanged to a desired counterion and then subjected to polymerization or may be ion-exchanged to a desired counterion after polymerization and then subjected to polymerization.

The polyester resin of the invention preferably contains the sulfonic acid salt skeleton component in 2 mole % or more and 20 mole % or less with respect to 100 mole of the polyfunctional (polyhydric) acid component. When the sulfonic acid salt skeleton component is contained in 2 mole % or more, the sulfonic acid salt site that can be electrolytically dissociated in water is large so that water dispersibility does not degrade. When the sulfonic acid salt skeleton component is contained in 20 mole % or less, storage stability that depends on the moisture to be adsorbed to the sulfonic acid salt site does not degrade.

Compound Containing Hetero Alicyclic Skeleton Component

The hetero alicyclic skeleton component of the invention is a component that constitutes the polyester resin.

Examples of a compound containing a hetero alicyclic skeleton component include a compound represented by the following General Formula (1) or (2).

[Chem. 1]

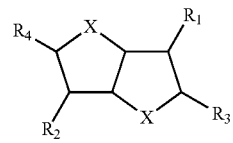

(1)

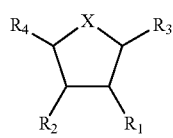

(2)

In General Formulae (1) and (2), X is selected from O, S, and SH; $R_1$ and $R_2$ each independently represent a functional group selected from the group consisting of a hydroxyl group, a hydroxyalkyl group, a hydroxyalkyl ether group, a carboxyl group, an amine group, an acid amide group, an alkoxy group, a carboxylic acid ester group, a carboxylic acid halide, a thiol group, and a phosphoric acid group, and $R_1$ and $R_2$ may be the same as or different from each other; and $R_3$ and $R_4$ each independently represent a functional group selected from the group consisting of a hydrogen atom, an alkyl group, an alkenyl group, a hydroxyl group, a hydroxyalkyl group, a hydroxyalkyl ether group, an aminoalkyl group, a carboxyl group, an amine group, an acid amide group, an alkoxy group, a carboxylic acid ester group, a carboxylic acid halide, a thiol group, and a phosphoric acid group, and $R_3$ and $R_4$ may be the same as or different from each other.

In General Formulae (1) and (2), from the viewpoint of ease of introducing a functional group, $R_1$ and $R_2$ are preferably a hydroxyl group, a carboxyl group, a carboxylic acid ester group, or a carboxylic acid halide. Further, from the viewpoint of availability of a raw material, $R_1$ and $R_2$ are preferably the same as each other.

From the viewpoint of ease of introducing a functional group, $R_3$ and $R_4$ are preferably a hydrogen atom, an alkyl group, an alkenyl group, a hydroxyl group, a hydroxyalkyl group, a carboxyl group, a carboxylic acid ester group, or a carboxylic acid halide. Further, from the viewpoint of availability of a raw material, $R_3$ and $R_4$ are preferably a hydrogen atom, a hydroxyl group, a hydroxyalkyl group, or a hydroxyalkyl ether group.

Specific examples of the compounds represented by General Formulae (1) and (2) include a sorbitan compound, a mannitan compound, D-isosorbide, L-isosorbide, and isomannide. From the viewpoint that the effect of the invention can be exerted and further from the viewpoint of availability, isosorbide and erythritane are preferable. These can be used alone or in combination of two or more kinds thereof.

The polyester resin of the invention contains a skeleton unit containing a hetero alicyclic skeleton component preferably in 1 mole % or more and 90 mole % or less, more preferably in 1 mole % or more and 85 mole % or less, and further preferably in 1 mole % or more and 80 mole % or less, with respect to 100 mole of the polyhydric acid component that constitutes the polyester resin. When the skeleton unit is contained in 1 mole % or more, grindability is excellent. Further, when the skeleton unit is contained in 90 mole % or less, generation of an oligomer or the like during polymerization can be suppressed and storage stability is excellent.

Further, when an atom other than carbon is introduced into the molecular structure by having a hetero skeleton structure, interaction force (such as hydrogen bonding strength, electrostatical interaction, or dipolar interaction) other than intermolecular force can be provided to the resin so that fixation behavior control of a toner can be performed. For example, when a nitrogen atom is introduced into X in General Formula (1) or (2), cationizing is easy to conduct, and the positive electrostatic property of a toner can be enhanced. The negative electrostatic property may be enhanced by introducing a sulfonic acid group after introduction of the nitrogen atom. Further, when an oxygen atom or a sulfur atom is introduced, dipolar interaction can be enhanced so that fixation strength of a toner is easy to provide.

Compound Containing Bisphenol A Alkylene Oxide Adduct Skeleton

The polyester resin of the invention may further contain a bisphenol A alkylene oxide adduct skeleton component in 1 mole % or more and 80 mole % or less with respect to 100 mole % of the acid component. By containing the above-described component, electrostatic property and strength of the resin can be improved (fixation strength of a toner can be improved). Further, by containing the above-described component, this can contribute to non-crystallization of the resin.

In order to introduce a bisphenol A alkylene oxide adduct skeleton unit into the polyester resin, the following compounds may be used as a polyalcohol component.

Specific examples thereof include bisphenol A alkylene oxide adducts such as polyoxyethylene-(2.0)-2,2-bis(4-hydroxyphenyl)propane, polyoxypropylene-(2.0)-2,2-bis(4-hydroxyphenyl)propane, polyoxypropylene-(2.3)-2,2-bis(4-hydroxyphenyl)propane, polyoxypropylene(2.2)-polyoxyethylene-(2.0)-2,2-bis(4-hydroxyphenyl)propane, polyoxypropylene(6)-2,2-bis(4-hydroxyphenyl)propane, polyoxypropylene(2.2)-2,2-bis(4-hydroxyphenyl)propane, polyoxypropylene-(2.4)-2,2-bis(4-hydroxyphenyl)propane, and polyoxypropylene(3.3)-2,2-bis(4-hydroxyphenyl)propane.

In the case of use for a toner, from the viewpoint of providing proper fixation strength and electrostatic property, it is preferable to use one kind or a combination of two or more kinds of polyoxypropylene-(2.3)-2,2-bis(4-hydroxyphenyl)propane and polyoxyethylene-(2.3)-2,2-bis(4-hydroxyphenyl)propane.

Trifunctional (Trivalent) or Higher Monomer Component

Of the monomers that constitute the polyester resin of the invention, a trivalent or higher monomer component is contained preferably in 1 mole % or more and 40 mole % or less, more preferably in 1 mole % or more and 35 mole % or less, and further preferably in 1 mole % or more and 30 mole % or less, with respect to 100 mole of the polyhydric acid component in the polyester resin. When the trivalent or higher monomer component is contained in 1 mole % or more, a cross-linked structure caused by a trivalent or higher monomer is present in the resin in some extent so that durability is excellent. Further, when the trivalent or higher monomer component is contained in 40 mole % or less, a drastic increase in viscosity during polymerization (gelation) can be suppressed so that polymerization stability is excellent. Further, the gel part causes an increase in particle diameter after water dispersion treatment.

A trivalent or higher acid (carboxylic acid) of trivalent or higher monomers is not particularly limited, but examples thereof include trimellitic acid, pyromellitic acid, 1,2,4-cyclohexane tricarboxylic acid, 2,5,7-naphthalene tricarboxylic acid, 1,2,4-naphthalene tricarboxylic acid, 1,2,5-hexane tricarboxylic acid, and 1,2,7,8-octane tetracarboxylic acid, or acid anhydrides or lower alkyl esters thereof.

Further, a trifunctional or higher alcohol of trifunctional or higher monomers is not particularly limited, but examples thereof include sorbitol, 1,2,3,6-hexa tetralol, 1,4-sorbitan, pentaerythritol, dipentaerythritol, tripentaerythritol, 1,2,4-butanetriol, 1,2,5-pentanetriol, glycerol, 2-methyl-1,2,3-propanetriol, 2-methyl-1,2,4-butanetriol, trimethylol propane, and 1,3,5-trihydroxy methyl benzene.

Of these, trimellitic acid or an acid anhydride thereof, pentaerythritol, and trimethylol propane are particularly preferable. These trifunctional or higher polyfunctional carboxylic acids and trifunctional or higher polyfunctional alcohols may be used alone or in combination of two or more kinds thereof. Particularly, trimellitic acid has a high boiling point and is less likely to become a substance that causes a volatile component generated from a toner. Thus, the trimellitic acid is used as a preferable substance.

Catalyst

The polyester resin of the invention is preferably obtained by performing polymerization using a titanium-based catalyst. The titanium-based catalyst has high reaction activity, and particularly, the esterification reaction time of the titanium-based catalyst is shorter than those of systems using no catalysts or systems using other catalysts so that the productivity of the resin is improved and the amount of a resin oligomer can be reduced. Thus, the particle diameter after water dispersion is likely to be uniform. As for catalysts other than the titanium-based catalyst, for example, a tin-based and antimony-based catalyst is typically a heterogeneous catalyst that is dispersed in a raw material, and this catalyst shows a tendency that when water dispersion treatment is performed, particles are likely to aggregate with this catalyst as a nucleus and the particle diameter suitable for a chemical toner is difficult to stably obtain. Further, there is a concern that those catalysts are environmental contamination materials so that use of those catalysts tends to be restricted. Thus, if the environmental load and influence on the aggregation are tried to be reduced by decreasing the amounts of those catalysts, the reactivity during polymerization degrades, which leads to a decrease in productivity due to the lengthening of the polymerization time.

Examples of the titanium-based catalyst include at least one titanium compound including a titanium alkoxide compound having an alkoxy group, titanium carboxylate, titanyl carboxylate, titanyl carboxylate salt, and a titanium chelate compound.

Examples of the titanium alkoxide compound having an alkoxy group include tetramethoxytitanium, tetraethoxytitanium, tetrapropoxytitanium, tetrabutoxytitanium, tetrapentoxytitanium, and tetraoctoxytitanium.

Examples of the titanium carboxylate compound include titanium formate, titanium acetate, titanium propionate, titanium octoate, titanium oxalate, titanium succinate, titanium maleate, titanium adipate, titanium sebacate, titanium hexanetricarboxylate, titanium isooctanetricarboxylate, titanium octanetetracarboxylate, titanium decanetetracarboxylate, titanium benzoate, titanium phthalate, titanium terephthalate, titanium isophthalate, titanium 1,3-naphthalenedicarboxylate, titanium 4,4-biphenyldicarboxylate, titanium 2,5-toluenedicarboxylate, titanium anthracenedicarboxylate, titanium trimellitate, titanium 2,4,6-naphthalenetricarboxylate, titanium pyromellitate, and titanium 2,3,4,6-naphthalenetetracarboxylate.

Examples of the titanyl carboxylate compound include titanyl benzoate, titanyl phthalate, titanyl terephthalate, titanyl isophthalate, titanyl 1,3-naphthalenedicarboxylate, titanyl 4,4-biphenyl dicarboxylate, titanyl 2,5-toluene dicarboxylate, titanyl anthracenedicarboxylate, titanyl trimellitate, titanyl 2,4,6-naphthalenetricarboxylate, titanyl pyromellitate, and titanyl 2,3,4,6-naphthalenetetracarboxylate.

The titanyl carboxylate salt compound is not particularly limited, but examples thereof include alkali metal (such as lithium, sodium, or potassium) salts or alkaline earth metal (such as magnesium, calcium, or barium) salts with respect to the above-described titanyl carboxylates.

Among these, tetrabutoxytitanium and tetrapropoxytitanium are preferable from the viewpoint of reactivity and the particle diameter of the water dispersion liquid. Further, in the case of using the titanium chelate compound, it is preferable to select a ligand from acetylacetone, ethyl acetoacetate, octylene glycol, triethanolamine, lactic acid, and ammonium lactate.

Examples of a polyfunctional (polyhydric) alcohol component other than the bis(2-hydroxyethyl)phthalate sulfonic acid salt skeleton component and the skeleton unit containing a hetero alicyclic skeleton component that constitute the polyester resin of the invention may include ethylene glycol, neopentyl glycol, propylene glycol, butanediol, polyethylene glycol, 1,2-propanediol, 1,4-butanediol, diethylene glycol, triethylene glycol, 1,4-cyclohexanedimethanol, cyclopentanediol, cyclohexanediol, hydrogenated bisphenol A, spiroglycol, dioxane glycol, dulcitol, and hexyd, and these can be used alone or in combination of two or more thereof. In particular, from the viewpoint of polymerization reactivity and ease of designing the Tg of the resin to be 40° C. or higher, ethylene glycol, 1,2-propanediol, and 1,4-cyclohexanedimethanol are preferable, and ethylene glycol and 1,2-propanediol are particularly preferable.

The content of the polyalcohol is preferably 60 mole % or more and 160 mole % or less, more preferably 60 mole % or more and 155 mole % or less, and particularly preferably 70 mole % or more and 150 mole % or less with respect to 100 mole of the polycarboxylic acid that constitutes the polyester resin of the invention, from the viewpoint of a balance between the glass transition temperature (Tg) and the softening temperature (T4).

When the content thereof is 60 mole % or more, the production stability of the polyester resin tends to become favorable. Further, when the content thereof is 160 mole % or less, Tg is likely to increase with respect to T4 and storage stability tends to become favorable.

Examples of the polyhydric acid (carboxylic acid) component that constitutes the polyester resin include components from terephthalic acid and isophthalic acid or lower alkyl esters thereof; and phthalic acid, sebacic acid, isodecyl succinic acid, dodecenylsuccinic acid, maleic acid, fumaric acid, itaconic acid, adipic acid, and furan dicarboxylic acid or monomethyl, monoethyl, dimethyl, diethyl esters or acid anhydrides thereof. Examples of the lower alkyl esters of terephthalic acid and isophthalic acid may include dimethyl terephthalate, dimethyl isophthalate, diethyl terephthalate, diethyl isophthalate, dibutyl terephthalate, and dibutyl isophthalate, but from the viewpoint of handling property and cost, terephthalic acid, isophthalic acid, and furan dicarboxylic acid are preferable. These aromatic dicarboxylic acids or lower alkyl esters thereof can be used alone or in combination of two or more kinds thereof. Further, since an aliphatic dicarboxylic acid component involves in basic characteristics of a toner such as fixability and blocking resistance, the aliphatic dicarboxylic acid component can be appropriately used in accordance with required performance in the range not impairing the object of the invention.

Furthermore, in the range not impairing the object of the invention, in order to adjust the number of terminal functional groups and improve dispersibility of other materials, monofunctional (monovalent) carboxylic acid or alcohol can also be used.

Examples of a monovalent carboxylic acid compound include an aromatic carboxylic acid having 30 or less carbon atoms, such as benzoic acid or p-methylbenzoic acid, an aliphatic carboxylic acid having 30 or less carbon atoms, such as stearic acid or behenic acid, and an unsaturated carboxylic acid having one or more unsaturated double bonds in the molecule, such as cinnamic acid, oleic acid, linoleic acid, or linolenic acid.

Further, examples of a monovalent alcohol compound include an aromatic alcohol having 30 or less carbon atoms, such as benzyl alcohol and an aliphatic alcohol having 30 or less carbon atoms, such as oleyl alcohol, lauryl alcohol, cetyl alcohol, stearyl alcohol, or behenyl alcohol.

The polymerization temperature is preferably in a range of 180° C. or higher and 280° C. or lower and more preferably 200° C. or higher and 270° C. or lower. When the polymerization temperature is 180° C. or higher, there is a tendency that productivity becomes favorable. When the polymerization temperature is 280° C. or lower, there is a tendency that decomposition of the resin and production of byproducts such as odor-causing volatile components can be suppressed.

The pH of slurry at the time of being charged for polymerization is, from the viewpoint of decomposition reaction during polymerization, preferably pH 4 or more and pH 8 or less. When the pH is less than 4, generation of oil components during esterification reaction is observed and easily occurs in accordance with dehydration of secondary and tertiary glycols so that a desired polyester resin is not obtainable. Further, when the pH is 9 or more, hydrolysis reaction of the obtained polyester resin easily proceeds in a preferred polymerization temperature region, and as a result, there is a tendency that a desired polyester resin is not obtainable.

Further, to determine when to finish polymerization of the polyester resin to be obtained, the condensation reaction may be conducted until the torque of the stirring blade reaches a value representing a desired softening temperature. Incidentally, terminating of polymerization indicates that stirring in the reaction apparatus is stopped, the inside of the apparatus is adjusted to normal pressure, the reaction product is taken out from the lower part of the apparatus by pressurizing the inside of the apparatus with nitrogen, and then the reaction product is cooled to 100° C. or lower.

Furthermore, in the invention, the polyester resin can also be polymerized by adding, as necessary, a release agent component together with the above-described components in the range not impairing the effect of the invention. By performing polymerization with addition of the release agent component, there is a tendency that fixability and wax dispersibility of a toner are improved.

Further, in order to achieve polymerization stability of the polyester resin, a stabilizer may be added. Examples of the stabilizer include hydroquinone, methyl hydroquinone, and a hindered phenol compound.

The glass transition temperature (Tg) of the polyester resin of the invention is preferably 40° C. or higher and lower than 85° C. In the case of using the polyester resin for a toner, from the viewpoint of storage stability, the glass transition temperature is preferably 45° C. or higher, and from the viewpoint of low-temperature fixability, the glass transition temperature is preferably 83° C. or lower. The glass transition temperature is particularly preferably 48° C. or higher and 80° C. or lower.

Further, the softening temperature of the polyester resin for a toner of the invention is preferably 80° C. or higher and 160° C. or lower, more preferably 80° C. or higher and 155° C. or lower, and further preferably 80° C. or higher and 150° C. or lower. When the softening temperature is 80° C. or higher, in the case of using the polyester resin for a toner, durability is excellent, and when the softening temperature is 160° C. or lower, low-temperature fluidity is excellent.

Further, the acid value of the polyester resin of the invention is preferably 1 mg KOH/g or more and 90 mg KOH/g or less, more preferably 1 mg KOH/g or more and 85 mg KOH/g or less, and further preferably 1 mg KOH/g or more and 80 mg KOH/g or less. When the acid value is 1 mg KOH/g or more, electrostatic property becomes favorable. When the acid value is 90 mg KOH/g or less, moisture absorption can be suppressed.

The peak molecular weight of the polyester resin of the invention in gel permeation chromatography (GPC) is, from the viewpoint of durability and fixability, preferably 1,000 or more and 300,000 or less, more preferably 1,000 or more and 30,000 or less, and further preferably 1,000 or more and 10,000 or less.

The polyester resin of the invention may also show crystallinity. The crystallinity of the resin is defined that the resin has a melting point peak as measured with one kind of resin using a differential scanning calorimetric measurement apparatus (DSC) according to JIS K7121. The melting peak temperature may be, for example, 50° C. or higher and 100° C. or lower, and is desirably 60° C. or higher and 90° C. or lower.

Method for Producing Polyester Resin

The polyester resin of the invention can be polymerized in the presence of at least one kind of a monomer selected from the compounds represented by General Formulae (1) and (2).

Method for Producing Toner

A toner containing the polyester resin of the invention can be produced by a known method. Examples of the known method include a method for producing a toner (chemical method) in which a resin and substances to be blended are dispersed in an aqueous medium and granulated in the aqueous medium, the solvent is then removed therefrom, and the granules are washed and dried to obtain toner particles, and then inorganic particles are added to the toner particles thus obtained as necessary.

The chemical method includes a step of preparing a resin particle dispersion liquid in which particles of the polyester resin of the invention are dispersed and a step of forming aggregate particles, and is to heat an aggregate particle dispersion liquid in which aggregate particles are dispersed and to fuse and coalesce the aggregate particles, thereby forming toner particles.

Hereinafter, respective steps will be described.

In the step of preparing a resin particle dispersion liquid in which particles of the polyester resin of the invention are dispersed, the aqueous medium and the resin of the invention are charged to have a desired solid content and the resultant product is warmed to Tg of the resin or higher to prepare a resin particle dispersion liquid. As the aqueous medium, for example, water, such as distilled water or ion-exchange water, and the like are exemplified. As an additive to be added to the water dispersion, an inorganic salt or alcohol having 6 or more and 16 or less carbon atoms may be added in the range not impairing the performance of a toner.

In a case where the particle diameters in the resin particle dispersion liquid are arranged, for example, a general dispersing method using a rotary shearing homogenizer, a ball mill having media, a sand mill, a Dyno mill, or the like is exemplified.

The volume average particle diameter of the polyester resin particles in the resin particle dispersion liquid is, for example, in a range of 0.01 μm or more and less than 2 μm. When the volume average particle diameter is less than 0.01 μm, the amount of the aggregating agent is likely to increase in the step of forming aggregate particles. When the volume average particle diameter is 2 μm or more, the number of particles for obtaining a desired toner particle diameter is small and it is difficult to uniformly mix materials.

Incidentally, the volume average particle diameter of the polyester resin particles is measured by a laser diffraction type particle size distribution measuring apparatus (LA-920, manufactured by HORIBA, Ltd.).

The content (solid content) of the polyester resin particles contained in the resin particle dispersion liquid is, for example, preferably 5 mass % or more and 50 mass % or less, more preferably 10 mass % or more and 40 mass % or less, and further preferably 15 mass % or more and 35 mass % or less. When the content is within 50 mass %, the dispersion liquid is less likely to be thickened and operability does not significantly deteriorate. When the content is 5 mass % or more, it is easy to form particles in the aggregation step, and for example, productivity of a chemical toner can be improved.

For example, a colorant dispersion liquid and a release agent dispersion liquid are also prepared in the same manner as in the resin particle dispersion. An aqueous medium used when the colorant dispersion liquid and the release agent dispersion liquid are prepared contains water as a main component, and from the viewpoint of environmental conservation, the content of water is preferably 80 mass % or more in the aqueous medium. Examples of a component other than water include organic solvents, which can be miscible with water, such as methanol, ethanol, isopropanol, butanol, acetone, methyl ethyl ketone, and tetrahydrofuran.

Further, when the colorant dispersion liquid and the release agent dispersion liquid are prepared, in order to stabilize the dispersion state of particles, neutralization treatment may be performed or a surfactant may be added, as necessary.

As a basic compound used in the neutralization treatment, any of an inorganic basic compound and an organic basic compound may be used. Examples of the inorganic basic compound include alkali metal hydroxides, such as sodium hydroxide, potassium hydroxide, and lithium hydroxide, or weak acid salts such as carbonic acid salt and an acetic acid salt, or partially neutralized salts thereof, and ammonia.

Examples of the organic basic compound include alkylamines such as methylamine, dimethylamine, trimethylamine, ethylamine, diethylamine, and triethylamine, alkanolamines such as diethanolamine, and fatty acid salts such as sodium succinate and sodium stearate. One kind of these basic compounds may be used alone or two or more kinds thereof may be used in combination.

Examples of the surfactant include an anionic surfactant such as sodium dodecylbenzenesulfonate or sodium octadecylsulfate; a cationic surfactant such as laurylamine acetate or lauryltrimethylammonium chloride; an ampholytic surfactant such as lauryldimethylamine oxide; and a nonionic surfactant such as polyoxyethylene alkyl ether. Among these, from the viewpoint of emulsion stability and the like, an anionic surfactant and a nonionic surfactant are preferable, and an anionic surfactant is more preferable. One kind of these surfactants may be used alone or two or more kinds thereof may be used in combination.

Further, a volume average particle diameter, a dispersing method, and a content of particles of each of colorant particles dispersed in the colorant dispersion liquid and release agent particles dispersed in the release agent dispersion liquid are the same as those of resin particles dispersed in the resin dispersion liquid.

As for the aggregate particle formation step, a colorant particle dispersion liquid and a release agent dispersion liquid are mixed with the resin particle dispersion liquid. In the dispersion liquid mixture, polyester resin particles, colorant particles, and release agent particles are subjected to hetero aggregation to form aggregate particles which have a particle diameter close to a target particle diameter of a toner and contain the resin/the colorant/the release agent. For example, an aggregating agent is added to the dispersion liquid mixture and the pH of the dispersion liquid mixture is adjusted to a pH of about 2 or more and 5 or less that is acidic condition. After a dispersion stabilizer is added as necessary, the dispersion liquid mixture is heated from the glass transition temperature of the resin particles to 80° C. to aggregate particles dispersed in the dispersion liquid mixture, thereby forming aggregate particles. Further, aggregate particles may be formed in such a manner that an aggregating agent is added under a room temperature condition of about of 25° C. while the dispersion liquid mixture is stirred with a rotary shearing homogenizer, the pH of the dispersion liquid mixture is adjusted to a pH of about 2 or more and 5 or less that is acidic condition, and after a dispersion stabilizer is added as necessary, the above-described heat treatment is performed.

As an example of the aggregating agent, an aggregating agent exhibiting salting-out action is preferable, and examples thereof include a surfactant having a polarity opposite to the polarity of the surfactant used as a dispersant to be added to the dispersion liquid mixture, an inorganic metal salt, and a divalent or higher metal complex.

Examples of the inorganic metal salt include metal salts such as calcium chloride, calcium nitrate, magnesium chloride, zinc chloride, aluminum chloride, and aluminum sulfate.

Further, a water-soluble chelating agent may be used. Examples of the chelating agent include tartaric acid, citric acid, and ethylenediamine tetra acetic acid (EDTA). The amount of the chelating agent added is, for example, in a range of 0.01 part by mass or more and 5.0 parts by mass or less and may be 0.1 part by mass or more and less than 3.0 parts by mass, with respect to 100 parts by mass of the resin particles.

The amount of the aggregating agent used is, from the viewpoint of aggregation capability and storage stability of a toner, preferably 0.01 part by weight or more and 20 parts by weight or less, more preferably 0.01 part by weight or more and 15 parts by weight or less, and further preferably 0.01 part by weight or more and 10 parts by weight or less, with respect to 100 parts by weight of the resin/the colorant/the release agent. When the amount of the aggregating agent used is in the above ranges, it is preferable that an aggregating agent is dissolved in an aqueous medium and then added under stirring and it is preferable to perform sufficient stirring during addition of the aggregating agent and after finishing addition of the aggregating agent.

Next, the aggregate particle dispersion liquid in which aggregate particles are dispersed is heated from the glass transition temperature of the polyester resin to about 80° C. to fuse and coalesce the aggregate particles to form toner particles. The toner particles formed in the solution are subjected to a washing step, a solid-liquid separation step, and a drying step that are known, thereby obtaining toner particles in a dry state.

In the washing step, it is preferable to sufficiently perform displacement washing with ion-exchange water from the viewpoint of electrostatic property. Further, the solid-liquid separation step is not particularly limited, but from the viewpoint of productivity, suction filtration, pressure filtration, and the like are preferable. Furthermore, in the drying step, from the viewpoint of productivity, freeze drying, flash jet drying, fluidized drying, vibration-type fluidized drying, and the like are used.

An external additive is added to the finally-obtained toner particles in a dry state and mixed to produce a toner. Mixing is performed, for example, by a blender, a Henschel mixer, or the like. Further, as necessary, coarse particles of the toner are removed by using a vibration classifier or the like to obtain a toner showing a desired particle size distribution.

Hereinafter, the invention will be described in more detail by means of Examples and Comparative Examples. Further, evaluation was conducted by the following method.

Glass Transition Temperature (Tg)

A glass transition temperature was measured by using a differential scanning calorimeter (DSC-60, manufactured by Shimadzu Corporation) and obtained as a value at the intersection of the baseline and the tangent of endothermic curve in a chart at a temperature increase rate of 5° C./min. In an aluminum pan, 10 mg±0.5 mg of a measurement sample was weighed, and melted for 10 minutes at a temperature of 100° C. higher than the glass transition temperature. Then, the measurement was conducted using the sample subjected to rapid cooling treatment using dry ice.

Softening Temperature (T4)

A temperature was measured using a flow tester (CFT-500D, manufactured by Shimadzu Corporation) when a 4 mm-long amount is flowed out of 1.0 g of a resin sample through a 1 mmφ×10 mm nozzle under conditions of a load of 294 N and a constant velocity temperature increase at a temperature increase rate of 3° C./min.

Acid Value (AV)

About 0.2 g of a sample was accurately weighed in a branched Erlenmeyer flask (A (g)), 10 ml of benzyl alcohol was added, and heat was applied to a resin for 15 minutes by a 230° C. heater to melt the resin under a nitrogen atmosphere. After the resin was cooled to room temperature, 10 ml of benzyl alcohol, 20 ml of chloroform, and a few drop of a phenolphthalein solution were added and titrated by using 0.02N KOH solution (titration volume=B (ml), strength of KOH solution=p). A blank measurement was similarly conducted (titration volume=C (ml)), and the acid value was calculated according to the following equation.

Acid value (mg KOH/g)=$(B-C)\times 0.02 \times 56.11 \times p \div A$

Molecular Weight: Peak Molecular Weight (Mp)

The peak molecular weight (Mp) in terms of standard styrene was determined from the retaining time corresponding to the peak value in the obtained elution curve, by a GPC method. Incidentally, the peak value of the elution curve is a value at the relative maximum point of the elution curve. When there are two or more relative maximum values, the peak value is where the elution curve is the maximum.

Device: HLC8020, manufactured by Toyo Soda Manufacturing Co., Ltd.
Column: three columns, TSKgel GMHXL, manufactured by Toyo Soda Manufacturing Co., Ltd. (column size: 7.8 mm (ID)×30.0 cm (L)) connected in series
Oven temperature: 40° C.
Eluent: THF
Sample concentration: 4 mg/10 mL
Filtration condition: sample solution was filtrated by a 0.45 µm Teflon (registered trademark) membrane filter
Flow rate: 1 mL/min
Injection amount: 0.1 mL
Detector: RI
Standard polystyrene samples for forming a calibration curve: TSK standard manufactured by Toyo Soda Manufacturing Co., Ltd., A-500 (molecular weight: $5.0\times 10^2$), A-2500 (molecular weight: $2.74\times 10^3$), F-2 (molecular weight: $1.96\times 10^4$) F-20 (molecular weight: $1.9\times 10^5$), F-40 (molecular weight: $3.55\times 10^5$), F-80 (molecular weight: $7.06\times 10^5$), F-128 (molecular weight: $1.09\times 10^6$), F-288 (molecular weight: $2.89\times 10^6$), F-700 (molecular weight: $6.77\times 10^6$), F-2000 (molecular weight: $2.0\times 10^7$)

Analysis of Resin Composition

A sample for NMR measurement was prepared by being dissolved in deuterochloroform.
The analysis was conducted using a superconducting nuclear magnetic resonance apparatus.
Device: ECS-400 superconducting FT-NMR manufactured by JEOL Ltd.
Magnet: JMTC-400/54/SS superconducting magnet
Observation frequency: $^1H$ 400 MHz, $^{13}C$ 100 MHz
Solvent: deuterochloroform solution
Temperature: 35° C.
Number of integrations: $^1H$: 16 times, $^{13}C$: 1024 times
$^1H$-NMR and $^{13}$-NMR were measured, and the percentage of [the compound (1), X in the compound (1) being an element other than C] containing the bis(2-hydroxyethyl) phthalate sulfonic acid salt and the hetero alicyclic skeleton component was determined from the integrated intensity ratio of each peak assigned to constituent units, and it was confirmed that there was no difference from the charged composition.

Quantitative Determination of S and Na

A combustion flask method was used as pre-treatment. Specifically, about 0.01 g (accurately weighed) of a sample was weighed with filter paper for weighing a sample, and the sample was combusted in a combustion flask. About 0.01 g (accurately weighed) of a sample was weighed with filter paper for weighing a sample, and the sample was combusted in a combustion flask. The sample was absorbed in a hydrogen peroxide solution. For S, the obtained solution was used without any change and then ion chromatography measurement was performed. For Na, 1% nitric acid was added to a container and then measurement was performed with an ICP emission spectrometry device. From these results, the proportion of the bis(2-hydroxyethyl)phthalate sulfonic acid salt was obtained, and it was confirmed that there was no difference from the charged composition.

Ion Chromatography Measurement Condition

Device: ICS-1500 manufactured by Dionex
Column: AS14A
Eluent: $Na_2CO_3$ 8 mmol/L; $NaHCO_3$ 1 mmol/L
Flow rate: 1.0 ml/min
Injection amount: 25 µl
Detector: electrical conductivity, current value 45 mA
Column•cell temperature: 35° C.

ICP Emission Spectrometry Measurement Condition

Device: iCAP6500 manufactured by Thermo Fisher Scientific Inc.
RF power: 750 W
Pump flow rate: 50 rpm
Auxiliary gas flow rate: 1 L/min
Nebulizer gas flow rate: 0.5 L/min
Coolant gas flow rate: 12 L/min
Purge gas flow rate: normal
Measurement wavelength: 588.995 (nm)

Water Dispersibility

Water dispersibility was determined from the volume median particle size of a resin dispersion liquid obtained by the following operation and the number of peaks. First, 2 g of a resin was accurately weighed in a standard bottle attached with a lid, and 8 g of distilled water was added thereto. The standard bottle containing the resin and the distilled water was inverted and shaken up every 1 hour under a constant temperature condition of 80° C. When coarse particles were not visually recognized on the bottom of the bottle during the bottle being shaken up, dispersion treatment was performed for 10 minutes at 50° C. and an output of 100% by using an ultrasound instrument (UT-206H, manufactured by SHARP CORPORATION).

The particle diameter and the particle size distribution of the obtained water-dispersible polyester resin are measured by using a laser diffraction type particle size distribution measuring machine (product name: "LA-920" manufactured by HORIBA, Ltd.). According to the operation manual of the device, by using a flow cell for measurement, distilled water is added into the cell, a relative refractive index is selectively set to 1.20, the particle diameter basis is set to the volume basis, and then adjustment of the optical axis, fine adjustment of the optical axis, and blank measurement are performed. Next, a polyester water dispersion liquid is added until the concentration reaches a transmittance range of 70% or more and 90% or less, ultrasonic treatment is performed for 1 minute at an intensity of 5, and then measurement of the particle size distribution of the resin particles is performed. The volume median particle size is a particle diameter (median size) corresponding to cumulative value 50% of the volume distribution basis.

A (good): The volume median particle size is less than 1 µm, and only one peak of the particle size distribution is recognized in a range of 0.02 µm or more and 2000 µm or less.

B (poor): The volume median particle size is 1 µm or more or two or more peaks of the particle size distribution are recognized in a range of 0.02 µm or more and 2000 µm or less.

Grindability

Grindability was evaluated by determining a residual ratio of a resin on a mesh. Herein, the resin residual ratio is a value obtained as follows. A resin subjected to a typical pulverization step was sieved, resin powder passing through a sieve having a mesh size of 2.0 mm or more and 2.5 mm or less was used. 10.00 g of this resin powder was accurately weighed, pulverized for 10 seconds by a pulverizer, Trio Blender (manufactured by Trio Science Co.), and then sieved with a sieve having a mesh size of 1.0 mm. The weight (A) g of the resin passing through the sieve was accurately weighed, and a passing ratio was obtained from the value of A. This operation was performed three times. The obtained values were averaged and the average value was regarded as the resin residual ratio.

[(A) g/Weight (10.00 g) of the resin before pulverization]×100=Resin passing ratio(%)

The grindability was evaluated as follows on the basis of the obtained resin passing ratios.

A (remarkably good): The resin passing ratio is 80% or more.

B (good): The resin passing ratio is 60% or more and less than 80%.

C (usable): The resin passing ratio is 40% or more and less than 60%.

D (poor): The resin passing ratio is 40% or less.

Low-Temperature Fluidity

As for the low-temperature fluidity, the resin was evaluated by using a rotational rheometer (AR-2000ex, manufactured by TA Instruments).

Geometry: 25 mmφ parallel plate
GAP: 1 mm
Frequency: 1 Hz
Distortion: 0.01
Measurement temperature: 80° C. or higher and 240° C. or lower (temperature increased at 3° C./min)

Criteria are as follows using a storage elastic modulus (G' at 130° C.) that shows good correlation with low-temperature fixability of a toner.

A (very good): G' is 100 mPa or less.
B (good): G' is 100 mPa or more and less than 300 mPa.
C (usable): G' is 300 mPa or more and less than 1000 mPa.
D (poor): G' is 1000 mPa or more.

Storage Stability

Storage stability is evaluated as follows. A water dispersion (solid content: 20 wt %) is dried with a resin obtained by freeze-drying in the presence of an aggregating agent, 5 g±0.5 g of the resin is weighed on an aluminum plate and stored for 24 hours in a constant temperature-and-humidity machine (manufactured by Satake Chemical Equipment Mfg Ltd.) adjusted to a temperature of 40° C. and a humidity of 80%. As the aggregating agent, anhydrous aluminum sulfate is used and the aggregating agent is prepared by being diluted with distilled water to have a concentration of 0.3 wt %. The expression "in the presence of an aggregating agent" indicates that a 0.3 wt % aqueous aggregating agent solution is added dropwise into a container in which a water dispersion (solid content: 20 wt %) is stirred at a rotation number of 5000 rpm by using a IKA ULTRA-TURRAX T25 digital and a material in which 90% or more of solid content of the water dispersion is aggregated is used. The resin on the aluminum plate after being stored in the constant temperature-and-humidity machine was evaluated on the basis of a proportion of the resin passing through a sieve having a mesh size of 2 mm (by the following equation).

Passing ratio (wt %)=[Resin (g) passing through the 2-mm sieve/Resin (g) weighed in the 2-mm sieve]×100

A (very good): The passing ratio is 95 wt % or more.
B (good): The passing ratio is 90 wt % or more and less than 95 wt %.
C (usable): The passing ratio is 80 wt % or more and less than 90 wt %.
D (poor): The passing ratio is less than 80 wt %.

Example 1

Carboxylic acid, alcohol, and tetra-n-butoxytitanium at 500 ppm with respect to the whole carboxylic acid, each of which had a charged composition presented in Table 1, were fed into a reaction vessel equipped with a distillation column.

Next, increasing of the temperature was started to carry out heating until the temperature in the reaction system reached 265° C. While the temperature was maintained, esterification reaction was performed until no water was distilled from the reaction system. Next, the temperature in the reaction system was adjusted to 235° C. and the pressure in the reaction vessel was reduced to perform condensation reaction while polyalcohol was distilled from the reaction system.

To determine when to finish polymerization, the condensation reaction was performed until the torque of the stirring blade reached a value representing a desired softening temperature. Next, stirring in the reaction apparatus was stopped, the inside of the apparatus was adjusted to normal pressure, and the reaction product was taken out from the lower part of the apparatus by pressurizing the inside of the apparatus with nitrogen. The reaction product was cooled to 100° C. or lower to obtain a polyester resin. The evaluation result of polymerization stability is presented in Table 1 on the basis of the esterification reaction behavior and the condensation reaction behavior. The evaluation result of the characteristic value of the obtained resin having favorable polymerization stability is presented in Table 1.

Next, the obtained resin was coarsely pulverized by using a pulverizer equipped with a 3-mm mesh at a discharge port. The grindability was evaluated using this coarsely-pulverized product. Further, the product was finely pulverized by a pulverizer, Trio Blender (manufactured by Trio Science Co.) to obtain resin powder having an average particle diameter of 250 μm or more and 500 μm or less by using a classifier (through sieving). The water dispersibility was evaluated using this resin powder. Finally, 93 parts by mass of coarsely-pulverized resin 1, 3 parts by mass of a quinacridone pigment (E02, manufactured by Clariant) as a colorant, 1 part by mass of a negative charge control agent LR-147 (manufactured by Japan Cartlit Co., Ltd.), and 3 parts by mass of carnauba wax (manufactured by Toyo Petrolite Co., Ltd.) were mixed to form a powder mixture, and the powder mixture was melt-kneaded by using a twin-screw extruder (PCM-29: Ikegai Corp.) at an external temperature of 120° C. and duration in the extruder for 1 minute. After being coarsely pulverized, the powder was finely pulverized by a jet mill pulverizer to obtain fine powder having an average particle diameter of 5 μm by using a classifier. The low-temperature fluidity was evaluated using this finely-pulverized toner without any external additive.

The evaluation result is presented in Table 1.

Examples 2 to 7 and Comparative Examples 1 and 2

A polycarboxylic acid component, a polyalcohol component, and tetra-n-butoxytitanium at 500 ppm with respect to a polyhydric acid component, each of which had a charged composition presented in Table 1, were fed into a reaction vessel equipped with a distillation column to obtain each polyester resin by using the same method as in Example 1. The polymerization stability and the characteristic value of each of the obtained polyester resins are presented in Table 1. Evaluation was conducted in the same manner as in Example 1.

Synthesis Example

Erythritane used in Example 3 was synthesized by the following procedures and used as a monomer of a polyester resin. The erythritane was analyzed by gas chromatography (column: DB-5 manufactured by J&B Scientific Co., Ltd., length 30 m×inner diameter 0.53 mm, film thickness: 3 μm, injection temperature: 200° C., detector temperature: 250° C., column temperature and time: kept for 1 minute at 60° C., temperature increased at 10° C./min, kept at 250° C.).

In a 300 ml four-neck flask equipped with a Claisen tube wrapped with a heat insulation material and a thermometer, 214.0 g (1.75 mol) of erythritol and 21 g (0.18 mol) of 85% phosphoric acid were charged. Further, a Liebig condenser, a thermometer, a bifurcated adapter, a flask, a trap set to prevent blockage by frozen water, a vacuum pump, and a pressure regulator were connected. The flask was heated in an oil bath while the solution was stirred using a magnetic stirrer. When the inner temperature reached 135° C., a reduction of pressure was initiated by turning on the vacuum pump, and the pressure was gradually reduced. Erythritane produced and distilled by reaction and some water were condensed by the Liebig condenser and recovered in the flask attached to the bifurcated adapter. Water not condensed by the Liebig condenser was recovered in the trap cooled with liquid nitrogen. Vacuuming was stopped when 65 ml of the distilled liquid was recovered in the flask, 72.5 g (0.59 mol) of erythritol was supplied, and then the vacuum pump was turned on so as to restart recovery of erythritane. Thereafter, the supply of erythritol was repeated 13 times by performing the same operation, and then the reaction was continued until no erythritane was distilled. The amount of erythritol used was 1229.0 g (10.1 mol). The temperature of the reaction solution was 135° C. or higher and 145° C. or lower and the final pressure was 150 Pa.

The erythritane recovered in the flask was analyzed by gas chromatography to analyze the purity of erythritane. The amount of erythritane acquired including water was 1001.7 g and the purity thereof was 96%, and the yield thereof was 92%.

In Comparative Example 1, since a hetero alicyclic skeleton component was not contained as a constituent unit of the polyester resin, grindability was not sufficient.

In Comparative Example 2, since a bis(2-hydroxyethyl) phthalate sulfosodium salt component was not contained as a constituent unit of the polyester resin, water dispersibility was not sufficient.

TABLE 1

| | | Example 1 Resin 1 | Example 2 Resin 2 | Example 3 Resin 3 | Example 4 Resin 4 | Example 5 Resin 5 | Example 6 Resin 6 | Example 7 Resin 7 | Comparative Example 1 Resin 8 | Comparative Example 2 Resin 9 |
|---|---|---|---|---|---|---|---|---|---|---|
| Charged composition (parts by mole) | Terephthalic acid | 60 | 60 | 60 | 60 | 60 | 54 | 54 | 60 | 60 |
| | Isophthalic acid | 30 | 30 | 30 | 32 | 26 | 40 | 40 | 32 | 38 |
| | Trimellitic acid | 2 | 2 | 2 | 2 | 2 | | | 2 | 2 |
| Charged composition Alcohol component (parts by mole) | Ethylene glycol | 72 | 72 | 72 | 74 | 78 | 70 | 70 | 122 | 80 |
| | bis(2-Hydroxyethyl)phthalate sulfosodium | 8 | 8 | 8 | 6 | 12 | 6 | 6 | 6 | |
| | Erythritane | | | 45 | | | 45 | 45 | | |
| | Isosorbide | 45 | 45 | | 45 | 45 | | | | 45 |
| | Trimethylol propane | | | | | | 6 | 6 | | |
| Resin composition (parts by mole) | Terephthalic acid | 62 | 61 | 61 | 62 | 60 | 55 | 55 | 61 | 60 |
| | Isophthalic acid | 31 | 31 | 31 | 32 | 28 | 40 | 40 | 31 | 38 |
| | Trimellitic acid | 2 | 2 | 2 | 2 | 2 | | | 2 | 2 |
| Resin composition Alcohol component (parts by mole) | Ethylene glycol | 68 | 58 | 66 | 61 | 58 | 68 | 62 | 103 | 58 |
| | bis(2-Hydroxyethyl)phthalate sulfosodium | 5 | 6 | 6 | 4 | 10 | 5 | 5 | 6 | |
| | Erythritane | | | 35 | | | 40 | 38 | | |
| | Isosorbide | 43 | 43 | | 44 | 43 | | | | 43 |
| | Trimethylol propane | | | | | | 6 | 6 | | |
| Catalyst (with respect to acid | Tetrahydrofuran | 500 | 500 | 500 | 500 | 500 | 500 | 500 | 500 | 500 |

TABLE 1-continued

|  |  | Example 1 Resin 1 | Example 2 Resin 2 | Example 3 Resin 3 | Example 4 Resin 4 | Example 5 Resin 5 | Example 6 Resin 6 | Example 7 Resin 7 | Comparative Example 1 Resin 8 | Comparative Example 2 Resin 9 |
|---|---|---|---|---|---|---|---|---|---|---|
| component, ppA) | | | | | | | | | | |
| Resin physical property value | Tg/° C. | 53 | 78 | 62 | 58 | 70 | 63 | 74 | 53 | 75 |
| | T4/° C. | 99 | 125 | 118 | 120 | 123 | 125 | 155 | 126 | 120 |
| | acid value/mg KOH · g$^{-1}$ | 55 | 34 | 77 | 41 | 40 | 51 | 39 | 32 | 19 |
| | Peak molecular weight | 1500 | 2300 | 2100 | 2000 | 2200 | 2200 | 2500 | 3200 | 2500 |
| Evaluation | Grindability | | | | | | | | | |
| | Proportion (wt %) of being 1 mm or less | 87 | 68 | 79 | 70 | 70 | 77 | 63 | 35 | 75 |
| | Evaluation | A | B | B | B | B | B | B | D | B |
| Water dispersibility | Particle diameter (μm) of water dispersion liquid | 0.1 | 0.2 | 0.1 | 0.2 | 0.1 | 0.1 | 0.2 | 0.1 | Not dispersed |
| | Number of peaks | 1 | 1 | 1 | 1 | 1 | 1 | 1 | 1 | — |
| | Evaluation | A | A | A | A | A | A | A | A | B |
| Low-temperature fluidity | Storage elastic modulus (Pa at 130° C.) | 55 | 350 | 94 | 120 | 280 | 210 | 950 | 380 | 290 |
| | Evaluation | A | C | A | B | B | B | C | C | B |
| Storage stability | Transmittance (wt %) | 91 | 99 | 95 | 97 | 88 | 96 | 98 | 78 | Not dispersed, unevaluable |
| | Evaluation | B | A | A | A | C | A | A | D | D |

INDUSTRIAL APPLICABILITY

In the case of using the polyester resin of the invention in a toner, it is possible to provide a toner in which a balance between water dispersibility and grindability can be achieved and which is excellent in low-temperature fluidity and storage stability. In addition, it is possible to develop the toner to a water-based adhesive or coating material with respect to a polyester base material.

The invention claimed is:

1. A polyester resin comprising, in polyesterified form:
    a polyhydric alcohol repeating unit comprising ethylene glycol;
    a polycarboxylic acid repeating unit comprising terephthalate and isophthalate;
    a (2-hydroxyethyl)isophthalate sulfonic acid salt;
    an at least trivalent monomer; and
    a hetero alicyclic skeleton component in an amount of from 1 part by mole or more to less than 50 parts by mole with respect to 100 parts by mole of a repeating unit derived from the polycarboxylic acid in the polyester resin,
    wherein the ethylene glycol in an amount of 58 part by mole or more with respect to 100 parts by mole of a repeating unit derived from the polycarboxylic acid in the polyester resin,
    wherein the at least trivalent monomer is at least one selected from the group consisting of trimellitate, pyromellitate, pentaerythritol, glycerol, and trimethylol propane, the at least trivalent monomer being present in up to 6 parts by mole with respect to 100 parts by mole of the polycarboxylic acid repeating unit in the polyester resin,
    wherein the hetero alicyclic skeleton component is at least one selected from the group consisting of D-isosorbide, L-isosorbide, isomannide, and erythritane, and
    wherein the polyester resin has a glass transition temperature from 40-85° C.

2. The polyester resin of claim 1, comprising the isosorbide.

3. The polyester resin of claim 1, wherein a counterion of the bis(2-hydroxyethyl)isophthalate sulfonic acid salt comprises at least one selected from the group consisting of sodium, potassium, and lithium.

4. A toner comprising the polyester resin of claim 1.

5. A method for producing the polyester resin of claim 1, the method comprising:
    conducting a polymerization reaction in the presence of a mixture comprising polyhydric alcohol repeating unit, the polycarboxylic acid, repeating unit, the bis(2-hydroxyethyl)isophthalate sulfonic acid salt, and the hetero alicyclic skeleton component.

6. The polyester resin of claim 1, having a softening temperature in a range of from 80 to 160° C.

7. The polyester resin of claim 1, comprising the (2-hydroxyethyl)isophthalate sulfonic acid salt in an amount from 2 parts by mole or more and 20 parts by mole or less, with respect to 100 parts by mole of a repeating unit derived from the polycarboxylic acid.

8. The method of claim 5, wherein the mixture comprises the (2-hydroxyethyl)isophthalate sulfonic acid salt in a range of from 2 to 20 parts by mole, with respect to 100 parts by mole of polycarboxylic acid.

9. The method of claim 5, wherein the mixture comprises the trimellitate in more than 0 to 2 parts by mole, with respect to 100 parts by mole of polycarboxylic acid.

10. The method of claim 9, wherein the mixture comprises the trimethylol propane in more than 0 to 6 parts by mole, with respect to 100 parts by mole of polycarboxylic acid.

11. The method of claim 5, Wherein the mixture further comprises a release agent.

12. The polyester resin of claim 1, having an acid value in a range of from 1 to 90 mg KOH/g.

13. The polyester resin of claim 1, wherein the glass transition temperature is no more than 78° C.

14. The polyester resin of claim 1, wherein the glass transition temperature is no more than 74° C.

15. The polyester resin of claim 1, wherein the glass transition temperature is no more than 70° C.

16. The polyester resin of claim 1, comprising the trimellitate in more than 0 to 2 parts by mole, with respect to 100 parts by mole of polycarboxylic acid.

17. The polyester resin of claim 13, comprising the hetero alicyclic skeleton component in an amount from 37 parts by mole or more and less than 50 parts by mole with respect to 100 parts by mole of the repeating unit derived from the polycarboxylic acid.

18. The polyester resin of claim 1, wherein the polyhydric alcohol repeating unit further comprises at least one of 1,2-propanediol and 1,4-cyclohexanedimethanol.

19. The polyester resin of claim 1, wherein the polyester resin comprises no glycerol repeating unit.

20. The polyester resin of claim 1, comprising the pentaerythritol.

21. The polyester resin of claim 1, comprising the erythritane.

22. The polyester resin of claim 1, comprising the isomannide.

* * * * *